US 6,645,152 B1

(12) United States Patent
Jung et al.

(10) Patent No.: US 6,645,152 B1
(45) Date of Patent: *Nov. 11, 2003

(54) APPARATUS FOR THE INTRAVASCULAR ULTRASOUND-GUIDED PLACEMENT OF A VENA CAVA FILTER

(76) Inventors: Matthew T. Jung, 3809 Flowering Grove Ct., Louisville, KY (US) 40241; Hermann W. Kaebnick, 1023 Anchorage Woods Cir., Louisville, KY (US) 40223; Edward V. Kinney, 2600 S. Pope Lick Rd., Louisville, KY (US) 40299; Richard A. Mitchell, 12808 N. Osage Rd., Louisville, KY (US) 40223

( * ) Notice: Subject to any disclaimer, the term of this patent is extended or adjusted under 35 U.S.C. 154(b) by 0 days.

This patent is subject to a terminal disclaimer.

(21) Appl. No.: 10/216,947

(22) Filed: Aug. 12, 2002

Related U.S. Application Data

(63) Continuation-in-part of application No. 09/567,800, filed on May 9, 2002, now Pat. No. 6,440,077.
(60) Provisional application No. 60/137,311, filed on Jun. 2, 1999.

(51) Int. Cl.⁷ .................................................. A61B 8/14
(52) U.S. Cl. .................................................... 600/467
(58) Field of Search ................................ 600/407–471, 600/473; 606/159, 198, 167, 127, 113, 200, 160; 604/22, 104, 96, 106; 128/772, 898

(56) References Cited

U.S. PATENT DOCUMENTS

| | | |
|---|---|---|
| 4,793,348 A | 12/1988 | Palmaz |
| 4,917,097 A | 4/1990 | Proudian et al. |
| 5,147,379 A | 9/1992 | Sabbaghian et al. |
| 5,152,777 A | 10/1992 | Goldberg et al. |
| 5,180,376 A | 1/1993 | Fischell |
| 5,415,630 A | 5/1995 | Gory et al. |
| 5,571,086 A | 11/1996 | Kaplan et al. |
| 5,681,347 A | 10/1997 | Cathcart et al. |
| 5,722,972 A | 3/1998 | Power et al. |
| 5,749,848 A | 5/1998 | Jang et al. |
| 5,769,816 A | 6/1998 | Barbut et al. |
| 5,830,224 A | * 11/1998 | Cohn et al. ............... 606/167 |
| 5,836,969 A | 11/1998 | Kim et al. |
| 5,865,178 A | 2/1999 | Yock |
| 5,876,344 A | 3/1999 | Baker et al. |
| 5,893,869 A | 4/1999 | Barnhart et al. |
| 5,921,931 A | 7/1999 | O'Donnell et al. |
| 5,931,788 A | 8/1999 | Keen et al. |
| 5,938,615 A | 8/1999 | Eberle et al. |
| 6,080,178 A | 6/2000 | Meglin |
| 6,267,776 B1 | 7/2001 | O'Connell |
| 6,440,077 B1 * | 8/2002 | Jung et al. ............... 600/467 |

OTHER PUBLICATIONS

Walsh and Bettmann, Percutaneous Devices for Vena Cava Filtration, Current Therapy in Vascular Surgery, p. 945.

Oppat, Chiou, and Matsumura, Intravascular Ultrasound-Guided Vena Cava Filter Placement, J Endovasc Surg 1999, pp. 285–287, vol. 6.

(List continued on next page.)

Primary Examiner—Ali M. Imam
(74) Attorney, Agent, or Firm—Stites & Harbison, PLLC; David W. Nagle, Jr.

(57) ABSTRACT

An apparatus for the intravascular placement of a vena cava filter includes a flexible deployment sheath and an IVUC with an ultrasonic imaging element. These two components are joined together and oriented in a substantially parallel relationship with one another with the imaging components of the IVUC extending above or in front of the upper opening of the deployment sheath. Once the apparatus is appropriately positioned within the vena cava, as determined through ultrasonic imaging, a filter and its associated delivery system are inserted through the deployment sheath to the appropriate location for deployment.

18 Claims, 7 Drawing Sheets

OTHER PUBLICATIONS

A Method for Inserting Inferior Vena Cava Filters at Bedside in Multitrauma Patients, Vascular Surgery Outlook, 1999, pp. 17–18, vol. 12, No. 5, Thieme Medical Publishers, Inc.

Sing, Smith, Miles and Messick, Preliminary Results of Bedside Inferior Vena Cava Filter PLacement, Chest, Jul., 1998, pp. 315–316, vol. 114, No. 1.

Benjamin et al, Duplex ultrasound Insertion of Inferior Vena Cava Filters in Multitrauma Patients, The American Journal of Surgery, Aug. 1999, pp. 92–97, vol. 178.

Oshima, Itchhaporia and Fitzgerald, New Developments in Intravascular Ultrasound, Vascular Medicine, 1998, pp. 281–290, vol. 3.

Rose, Kinney, Valji, and Winchell, Placement of Inferior Vena Caval Filters in the Intensive Care Unit, Journal of Vascular and Interventional Radiology, Jan.–Feb. 1997, pp. 61–64, vol. 8.

Brigade Brachytherapy System Promotional Flier, EndoSonics Corporation, Rancho Cordova, CA, The Netherlands and Germany.

Simon Nitinol Filter Promotional Flier, C.R. Bard, Inc., Covington, Georgia.

Uren, Neal G., An Introduction to Intravascular Ultrasound, 1996, REMEDICA, Hooper House, Oxford, England.

* cited by examiner

APPARATUS FOR THE INTRAVASCULAR ULTRASOUND-GUIDED PLACEMENT OF A VENA CAVA FILTER

CROSS-REFERENCE TO RELATED APPLICATIONS

The present application is a continuation-in-part of U.S. Utility patent application Ser. No. 09/567,800, filed May 9, 2002, entitled METHOD AND APPARATUS FOR THE INTRAVASCULAR ULTRASOUND-GUIDED PLACEMENT OF A VENA CAVA FILTER now U.S. Pat. No. 6,440,077 an application claiming priority from U.S. Provisional Patent Application Ser. No. 60/137,311, filed Jun. 2, 1999. Each of the above-referenced applications is incorporated herein by reference.

BACKGROUND OF THE INVENTION

The present invention relates to an apparatus for the intravascular ultrasound-guided placement of vena cava filters, said filters often being necessary in the treatment of deep vein thrombosis.

A deep vein thrombosis is a medical condition wherein a blood clot, or thrombus, has formed inside a vein. Such a clot often develops in the calves, legs, or lower abdomen, but occasionally affects other veins in the body. This clot may partially or completely block blood flow, and, unlike clots in superficial veins, the clot may break off and travel through the bloodstream. Commonly, the clot is caused by a pooling of blood in the vein, often when an individual is bed-ridden for an abnormally long duration of time, for example, when resting following surgery or suffering from a debilitating illness, such as a heart attack or traumatic injury.

Deep vein thrombosis of the lower extremities is a serious problem because of the danger that the clot may break off and travel through the bloodstream to the lungs, causing a pulmonary embolism. This is essentially a blockage of the blood supply to the lungs that causes severe hypoxia and cardiac failure. It frequently results in death.

For many patients, anti-coagulant drug therapies may be sufficient to dissipate the clots.

For example, patients may be treated with anticoagulants such as heparin and with thrombolytic agents such as streptokinase. Heparin is available and marketed under such trade names as Heparin Lock™, a product of Abbott Laboratories of Abbott Park, Ill.; and Heparin Sodium™, a product of Pharmacia & Upjohn of Peapack, N.J. Streptokinase is available and marketed under such trade names as Streptase®, a product of Behringwerke Aktiengesellschaft of Frankfurt, Germany; and Kabikinase®, a product of Kabivitrum Aktiebolag of Stockholm, Sweden.

Unfortunately, some patients may not respond to such drug therapy or may not tolerate such therapy. For example, patients may have an acute sensitivity to heparin or may suffer from internal bleeding as a result of such drug therapies. Also, such drug therapies simply may be ineffective in preventing recurrent pulmonary emboli. In such circumstances, surgical procedures are required to prevent pulmonary emboli. Methods for prevention of primary or recurrent pulmonary emboli when anticoagulation therapies are ineffective are well-defined in the prior art. The current standard of therapy for prevention of pulmonary emboli in patients who are classified high-risk or are unable to be anticoagulated is percutaneous insertion and placement of an inferior vena cava filter device. A detailed discussion of the construction and use of such filters is contained in U.S. Pat. No. 5,893,869 issued to Barnhart, which is incorporated herein by reference. Additional information on such filters can also be found in an article entitled "Percutaneous Devices for Vena Cava Filtration" by Daniel E. Walsh and Michael Bettmann contained in *Current Therapy in Vascular Surgery* (3d ed. 1995) at pages 945–949; this article is also incorporated herein by reference.

Placement of these filters is usually accomplished using either the "femoral vein approach" or "jugular vein approach," although alternative approaches, including "axiliary vein approaches," may also be used. There have been a few reports of transabdominal ultrasound being used for placement of filters, but most prior art methods and approaches use fluoroscopy for placement of a guide wire and catheter, as well as for placement and deployment of the filter.

Such methods for placement and deployment of a filter also recommend the use of an intravenous dye with contrast angiography.

The fluoroscopy unit may be employed to aid in the placement of the filter in several different ways. For example, the patient is often brought to a operating room or special procedures room, and a fluoroscopy unit is used to identify bony landmarks, allowing the physician to choose the appropriate location for the filter by referencing the bony landmarks. When referencing bony landmarks, placement of the filter is usually done by referencing the lumbar third and fourth vertebrae, making an assumption that the renal veins will be higher than this. However, this method does not provide for an accurate definition of the vena cava size, identification of the position of a clot or thrombus in the vena cava, or accurate identification of the site of the renal veins. It is important to note that, regardless of the method employed in placing the filter, the filter must be placed below the renal veins.

A second and much more accepted method entails the use of a fixed C-arm or fluoroscopic C-arm guidance unit and intravenous contrast in an inferior venacavagram to define the size of the inferior vena cava, to identify the site of the renal veins, and to ascertain the presence or absence of clot at the site proposed for deployment of the filter device. Although this method is often performed in radiology or surgical suites, rather than intensive care units, a general discussion of this method is contained in an article entitled "Placement of Inferior Vena Caval Filters in the Intensive Care Unit" by Drs. Steven C. Rose, Thomas B. Kinney, Karim Valji, and Robert J. Winchell contained in the *Journal of Vascular and Interventional Radiology*, 8:61–64 (1997); this article is also incorporated herein by reference. Deployment of the filter is then performed per the percutaneous filter placement protocols based on the previously performed venacavagram findings. A distinct disadvantage of this method, however, is that the procedure must be performed in either a special x-ray suite or a specially equipped operating room. Thus, significant expense is involved in carrying out this procedure, especially considering that additional staff is often required for a special suite or an operating room. Moreover, the necessity of this specialized location necessitates the transport of an often critically ill or unstable patient from their hospital room to the site of x-ray equipment.

Co-pending U.S. application Ser. No. 09/567,800, which is incorporated herein by reference, describes an apparatus for addressing the disadvantages of prior art apparatus and methods. Specifically, U.S. application Ser. No. 09/567,800 describes an apparatus that combines commercially available surgical components into a unitary device for accurate and effective positioning and placement of a vena cava filter. A preferred embodiment of that apparatus comprises an outer sheath, an intravascular ultrasound catheter with an ultrasonic imaging element, a guide wire, and a vena cava filter that is to be deployed. The outer sheath, ultrasound catheter, and guide wire share a common central axis. The ultrasound catheter is enclosed by and is moveable relative to the outer sheath, and the guide wire is enclosed by and is moveable relative to the ultrasound catheter. In the stored position, the filter is secured between the outer sheath and the ultrasound catheter.

When the apparatus described in U.S. application Ser. No. 09/567,800 is introduced into a vein, the ultrasound catheter provides real-time imaging of the vein for identifying the appropriate location for placement of the filter. Once such a location has been identified, the outer sheath is drawn back relative to the ultrasound catheter, exposing the legs of the filter, allowing the legs of the filter to spring free and attach themselves to the wall of the vein. Such an apparatus and the use thereof obviates the need for cumbersome and specialized fluoroscopy equipment and/or an intravenous contrast, while also allowing filter placement to be performed bedside, substantially reducing the overall time and cost of the placement procedure.

Although the apparatus described in U.S. application Ser. No. 09/567,800 adequately addresses many of the problems and issues associated with prior art apparatus and methods, it is a paramount object to provide an alternate construction for an apparatus for intravascular placement of a filter that similarly does not require the use of cumbersome and specialized fluoroscopy equipment and/or an intravenous contrast, nor does it require the use of any specific filter or any specific filter delivery system.

This and other objects and advantages of the present invention will become apparent upon a reading of the following description.

SUMMARY OF THE INVENTION

The apparatus of the present invention combines commercially available surgical components into a unitary device for accurate and effective positioning and placement of a vena cava filter. A preferred embodiment of the apparatus of the present invention comprises a flexible deployment sheath and an intravascular ultrasound catheter ("IVUC") with an ultrasonic imaging element. These two components are joined together and oriented in a substantially parallel relationship with one another with the ultrasonic imaging element of the IVUC extending above or in front of the upper opening of the deployment sheath.

As the apparatus of the present invention is moved through the veins and into position for deployment of a filter, the positioning of the ultrasonic imaging element of the IVUC in front of the deployment sheath provides for a clear, unobstructed ultrasonic picture of the veins. The real-time ultrasonic imaging of the veins also allows for measurement of the inner diameter of the vena cava for appropriate placement of the filter, and provides a visual confirmation that there is no thrombus in the area selected for deployment. Once the apparatus is appropriately positioned within the vena cava, a filter and its associated delivery system are inserted through the deployment sheath to the appropriate location for deployment. In this regard, the deployment sheath serves as a conduit into the vena cava for deployment of the filter, and therefore the apparatus of the present invention can be used with virtually any existing filter and associated delivery system, provided that the inner diameter of the deployment sheath is adequate to accommodate insertion of the desired filter and its delivery system.

Such an apparatus and the use thereof obviates the need for cumbersome and specialized fluoroscopy equipment and/or an intravenous contrast, while also allowing filter placement to be performed bedside, substantially reducing the overall time and cost of the placement procedure.

DESCRIPTION OF THE PREFERRED EMBODIMENTS

The present invention is an apparatus for the intravascular ultrasound-guided placement of vena cava filters.

Figure 2:
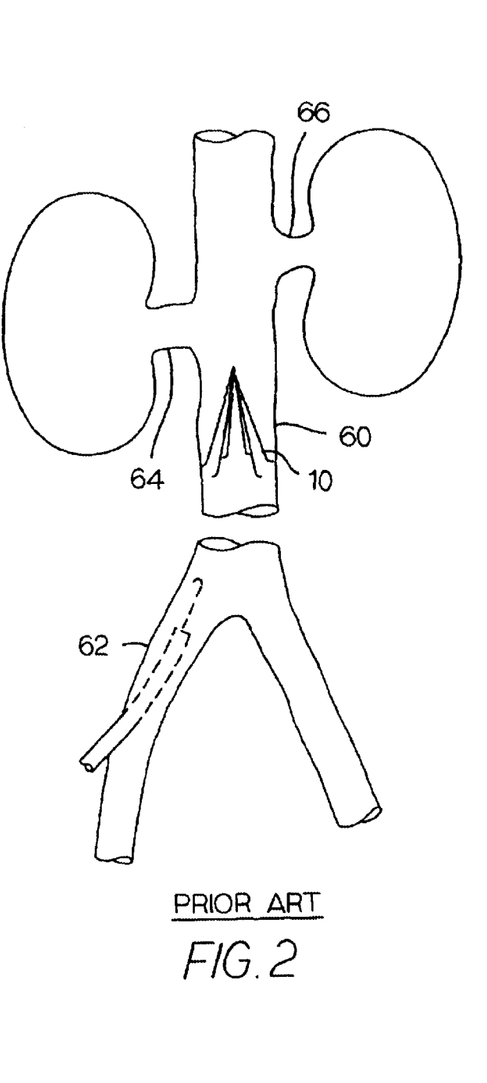
FIG. 2 illustrates the proper placement of a vena cava filter directly below the renal veins in the inferior vena cava.

FIG. 2 depicts the appropriate placement of a vena cava filter 10 directly below the renal veins 64, 66 in the inferior vena cava 60. Great care must be taken to define the anatomy of this area prior to deployment to avoid encroachment on the renal veins 64, 66 and to ascertain the absence or presence of clots in the vena cava 60. Also, the attending physician must ensure that the vena cava 60 has the appropriate inner diameter for receiving the filter, typically between 10 to 20 mm, and no greater than 28 mm.

Figures 3, 4:
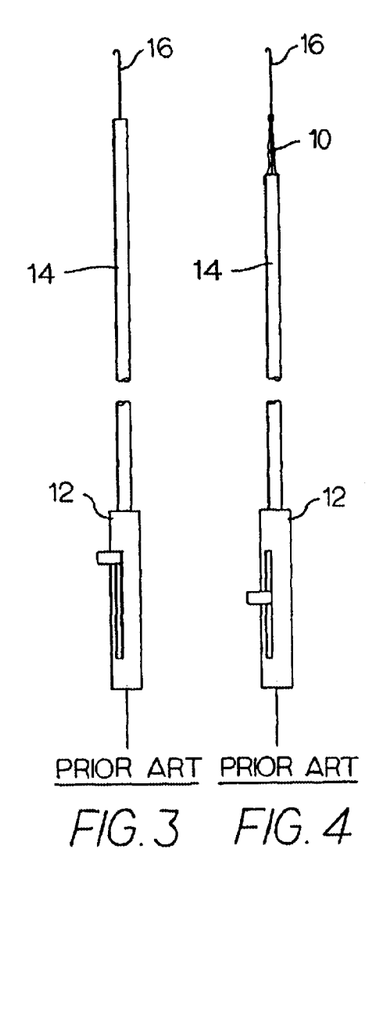
FIG. 3 is a side view of a prior art filter deployment device and associated guide wire wherein the filter is housed within a sheath catheter.
FIG. 4 is side view of the prior art filter deployment device of FIG. 3 wherein the filter is partially deployed.
Figure 5:
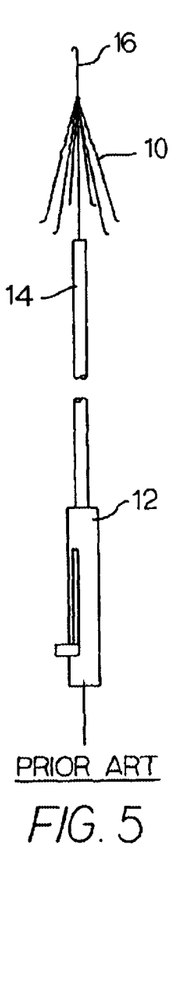
FIG. 5 is side view of the prior art filter deployment device of FIG. 3 wherein the filter is fully deployed.

FIGS. 3–5 show a typical prior art filter 10 and the deployment device 12 for placement of the filter 10. Generally, the deployment device 12 includes a sheath catheter 14 over a guide wire 16. The filter 10 to be deployed is loaded into the distal end of the sheath catheter 14. The catheter 14 is inserted into a vein, and then appropriately positioned using a fluoroscopy unit or other method, as described above. Once so positioned, the outer sheath of the catheter 14 is retracted, allowing the filter 10 to spring open and attach to the walls of the vein. The catheter 14 and guide wire 16 are then withdrawn and removed. Placement of these filters is usually accomplished using fluoroscopy and a contrast angiography. As described above, one common method entails the use of a fixed C-arm or fluoroscopic C-arm guidance unit and intravenous contrast in an inferior venacavagram to define the size of the inferior vena cava, to identify the site of the renal veins, and to ascertain the presence or absence of clot at the site proposed for deployment of the filter 10. Deployment is then performed per the percutaneous filter placement protocols based on the previously performed venacavagram findings.

Figure 6:
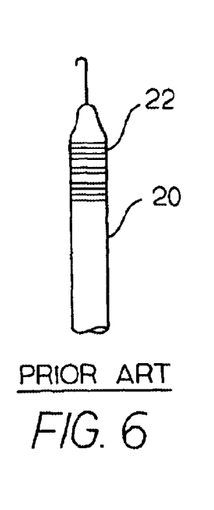
FIG. 6 is a side view of a prior art intravascular ultrasound catheter and associated guide wire.

FIG. 6 of the present application depicts a common prior art intravascular ultrasound catheter ("IVUC") 20. Such a catheter is commonly an extruded plastic sheath having a circumferential wall enclosing and protecting the internal wiring and circuitry of the IVUC 20. This particular IVUC includes a solid state imaging element 22. Such IVUCs 20 can provide high quality, real-time imaging of the internal walls of a blood vessel and thus are commonly used in the diagnosis and treatment of fully or partially blocked arteries of the heart, often through the use of an IVUC 20 in conjunction with a percutaneous transluminal coronary angioplasty (commonly referred to as "balloon angioplasty"). For a general discussion of intravascular ultrasound catheters and their use in angioplasty, see U.S. Pat. No. 5,749,848 issued to Jang, et al. and assigned to Cardiovascular Imaging Systems, Inc. of Sunnyvale, Calif. This patent is incorporated herein by reference.

Referring still to FIG. 6, the ultrasonic imaging element 22 that generates the cross-sectional imaging of a blood vessel is housed in the tip of the catheter 20. Signals from the ultrasonic imaging element 22, indicative of reflected ultrasonic waves, are transmitted through internal wires within the catheter 20 to a signal processor.

The design and construction of intravascular ultrasound catheters is well-known in the art. For example, one such IVUC is described in U.S. Pat. No. 4,917,097, issued to Proudian, et al. and assigned to the Endosonics Corporation of Cordova, Calif. This patent is incorporated herein by reference. The present invention does not seek to redesign or improve upon the construction of such catheters, whether they be solid state or mechanical in nature, but rather seeks to employ a intravascular ultrasound catheter in a new and unique apparatus. Indeed, it is contemplated that the apparatus and method of the present invention be carried out by using a commercially available IVUC, such as the EndoSonic® phased array solid state catheter with central wire or the ClearView Ultra™ Intravascular Ultrasound System manufactured and distributed Boston Scientific Corporation of Natick, Mass.

Figures 7, 7A, 8, 8A:
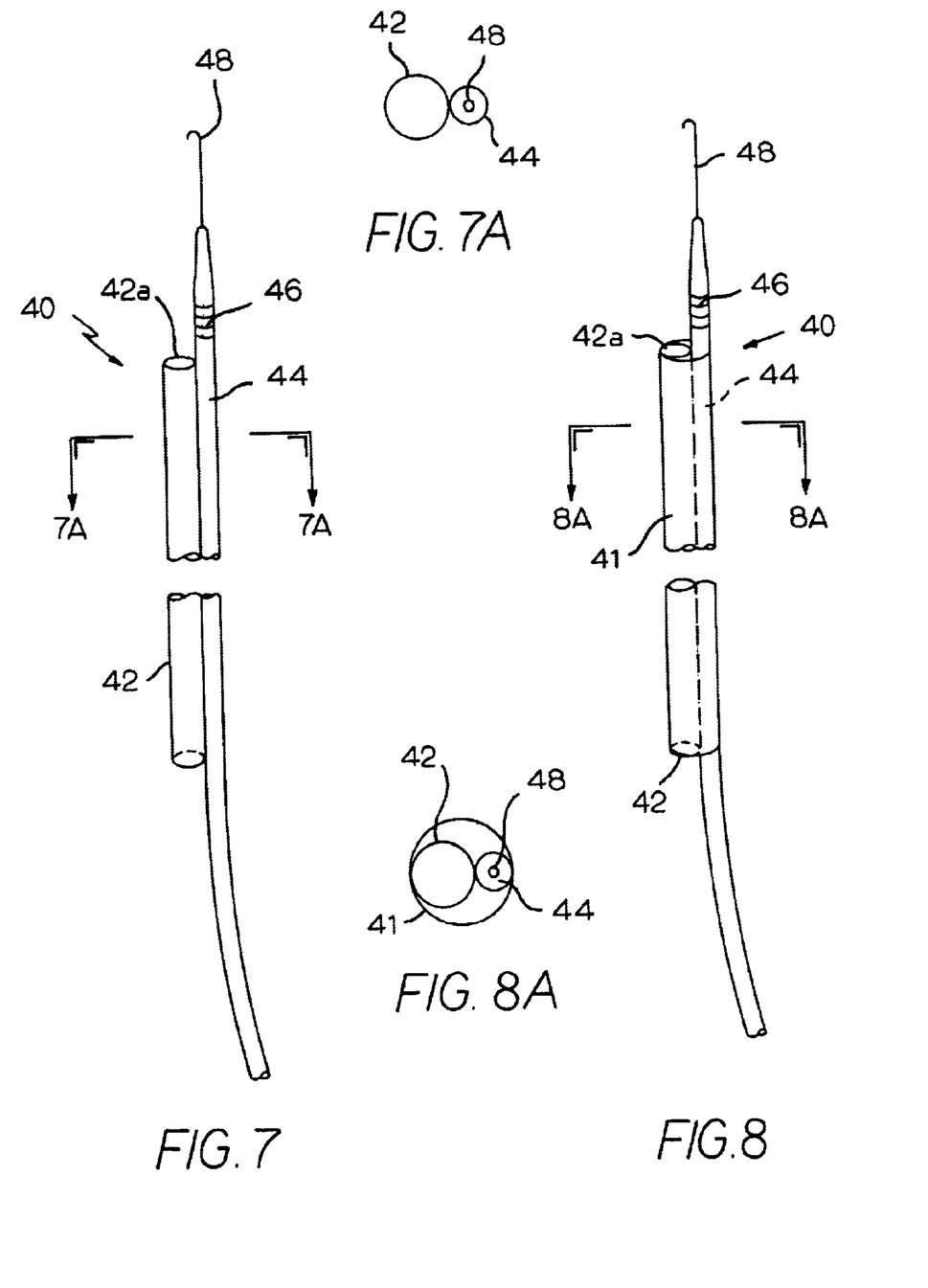
FIG. 7 is a side view of a first preferred embodiment of the apparatus of the present invention.
FIG. 7A is a sectional view of the preferred apparatus of FIG. 7, taken along line 7A—7A of FIG. 7.
FIG. 8 is a side view of a second preferred embodiment of the apparatus of the present invention.
FIG. 8A is a sectional view of the preferred apparatus of FIG. 8, taken along line 8A—8A of FIG. 8.

FIGS. 7 and 7A depict a first preferred embodiment of the apparatus of the present invention. This apparatus 40 combines commercially available surgical components into a unitary device for accurate positioning and placement of a vena cava filter. As shown in FIGS. 7 and 7A, this preferred apparatus 40 is comprised of a flexible deployment sheath (or lumen) 42 and an IVUC 44 with an ultrasonic imaging element 46. These two components are joined together along a portion of their respective lateral surfaces such that they are oriented in a substantially parallel relationship with one another with the ultrasonic imaging element 46 of the IVUC 44 extending above or in front of the upper opening 42a of the deployment sheath 42.

The deployment sheath 42 essentially serves as a conduit into the vena cava for deployment of a filter and is preferably a 6.0–12.0 Fr flexible sheath. However, it is understood that the diameter of the deployment sheath 42 can be widely varied to accommodate different filter delivery systems, as will be further described below.

The IVUC 44 preferably has a diameter of approximately 6.0 Fr. As shown, the IVUC 44 has a solid state imaging element 46, although a mechanical or rotating mirror imaging element could be used without departing from the spirit and scope of the present invention. Again, the present invention does not seek to redesign or improve upon the construction of ultrasonic catheters, whether they be solid state or mechanical in nature, but rather seeks to employ a intravascular ultrasound catheter in a new and unique apparatus.

Furthermore, as shown in FIGS. 7 and 7A, in this preferred embodiment, there is a guide wire 48 that extends through the IVUC 44. This guide wire 48 is preferably a J-tipped or curved wire with a Teflon® coating or similar lubricant. Such coating facilitates smooth movement of the guide wire 48 within a blood vessel, thereby minimizing the hazards of blood clot generation and trauma to internal tissues. In this preferred embodiment, the approximate diameter of this guide wire 48 is 0.035 inches, allowing it to be easily manipulated and passed through the IVUC 44. In this regard, the IVUC 44 has an annular cross-section and defines an inner diameter. This inner diameter is slightly greater than the outer diameter of the guide wire 48.

FIGS. 8 and 8A depict a second preferred embodiment of the apparatus of the present invention. As shown, and as with the embodiment depicted in FIGS. 7 and 7A, this alternate preferred embodiment is also comprised of a flexible deployment sheath 42 and an IVUC 44 with an ultrasonic imaging element 46. The difference is that, in this alternate preferred embodiment, the flexible deployment sheath 42 and the IVUC 44 are enclosed in an outer sheath 41.

Figure 1:
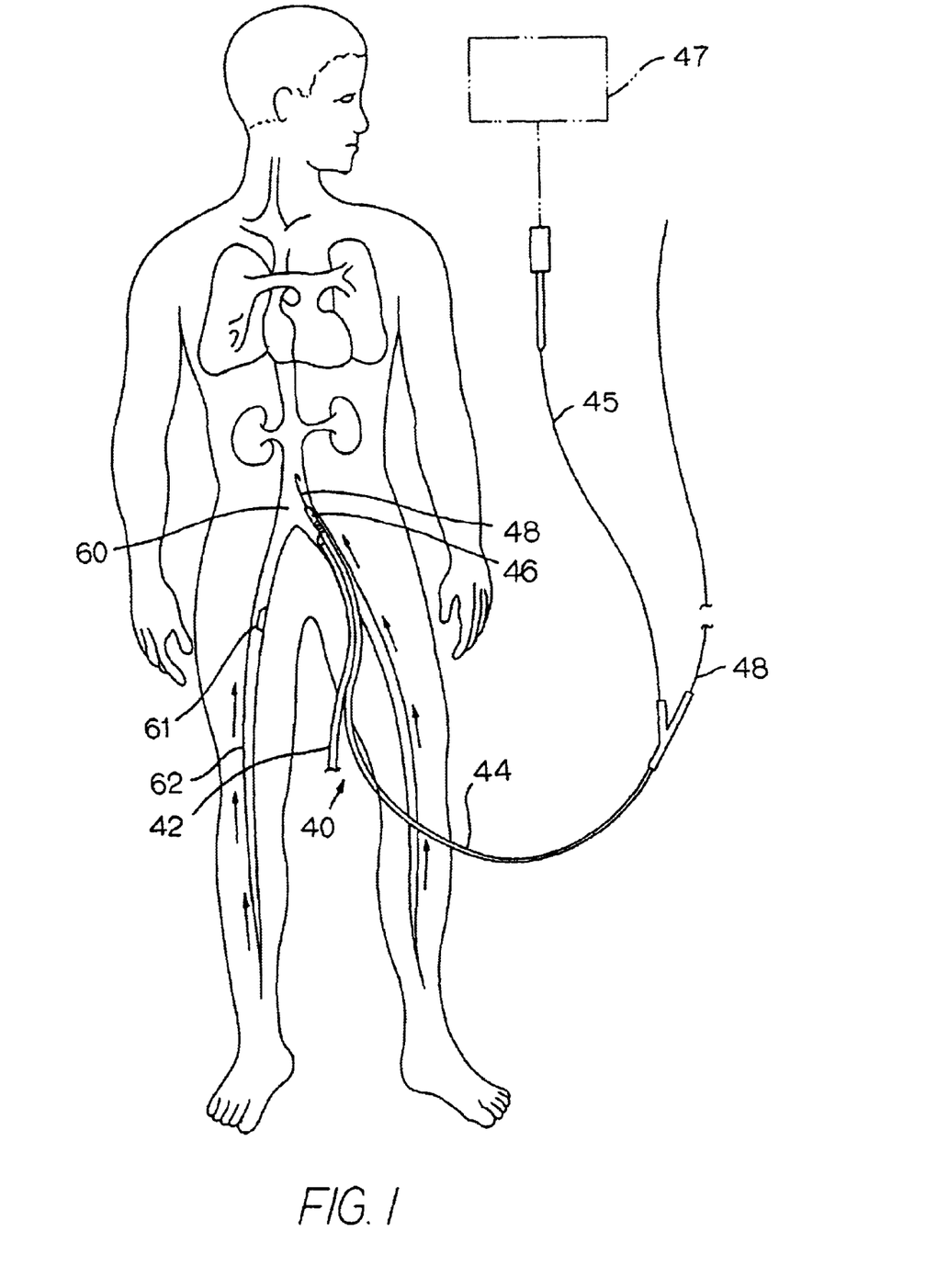
FIG. 1 illustrates a first preferred embodiment of the apparatus of the present invention as positioned in a vein for deployment of a vena cava filter.

A better understanding of the construction of the apparatus 40 of the present invention, specifically the embodiment depicted in FIGS. 7 and 7A, can be achieved through a review of the function and operation of the apparatus 40. Referring first to FIG. 1, a thrombus 61 is present in the right femoral vein 62. As indicated by the arrows, blood flows from the femoral veins 62 through the vena cava 60 toward the heart and lungs, and thus placement of a vena cava filter (not shown in FIG. 1) is necessary to prevent the thrombus 61 from traveling to the heart and lungs should it break free.

To deploy the vena cava filter using the preferred apparatus 40, the guide wire 48 is inserted into the vena cava 60, preferably using the Seldinger technique from the femoral position. Over the guide wire 48, the IVUC 44 and deployment sheath 42 are passed percutaneously through the femoral vein 62 and into the vena cava 60. Of course, the length of the apparatus 40 must be adequate to travel the requisite distance through the veins. In this regard, the deployment sheath 42 preferably has a length of 40–65 cm. As the IVUC 44 and deployment sheath 42 travel through the femoral vein 62 and into the vena cava 60, the ultrasonic imaging element 46 of the IVUC 44 provides a real-time ultrasonic picture of its passage, thereby assuring proper placement of the filter. In this regard, the ultrasonic signals received by the ultrasonic imaging element 46 are transmitted through internal wiring 45 of the IVUC 44 to an external signal processor (as indicated in phantom and by reference numeral 47 in FIG. 1). This real-time imaging of the veins also allows for measurement of the inner diameter of the vena cava 60 and provides a visual confirmation that there is no thrombus in the area selected for deployment of the filter. Finally, the ultrasonic imaging allows for extremely accurate identification of the position of the renal veins 64, 66 to further ensure appropriate placement of the filter. In this regard, it is preferred that the deployment sheath 42 and IVUC 44 are moved through the vena cava 60 past the renal veins 64, 66 so that the attending physician can view the portions of the vena cava 60 adjacent the renal veins 64, 66. The deployment sheath 42 and IVUC 44 are then drawn back to an appropriate position below the renal veins 62, 64 for deployment of the filter. After deployment of the filter, the preferred apparatus 40, sans the filter, is withdrawn from the vena cava 60.

Figures 9, 10:
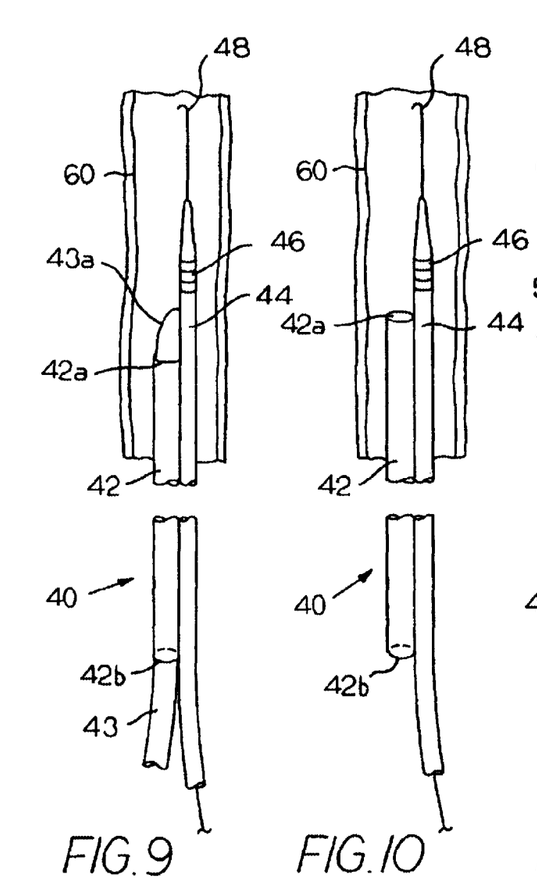
FIG. 9 illustrates the preferred apparatus of FIG. 7 being positioned in a vein for deployment of a vena cava filter, with an introducer contained within the deployment sheath of the apparatus.
FIG. 10 illustrates the preferred apparatus of FIG. 7 after withdrawal of the introducer from the deployment sheath of the apparatus.

FIGS. 9–13 illustrate, in greater detail, the deployment of a filter 50 using the preferred apparatus 40 described above. Referring first to FIG. 9, when the IVUC 44 and deployment sheath 42 are inserted and moved into position in the vena cava 60, it is preferred that an introducer 43 be contained within the deployment sheath 42 to provide additional rigidity to the apparatus 40 as it is inserted and moved within the vena cava 60, and also to eliminate any sharp edges associated with the upper opening 42a of the deployment sheath 42. In this regard, the preferred introducer 43 has a rounded, smooth distal end 43a.

As also shown in FIG. 9, the ultrasonic imaging element 46 of the IVUC 44 extends beyond the upper opening 42a of the deployment sheath 42, or in front of the deployment sheath 42. The positioning of the ultrasonic imaging element 46 of the IVUC 44 in front of the deployment sheath 42 provides for a clear, unobstructed ultrasonic picture of the femoral vein 62 and vena cava 60 as the preferred apparatus 40 is moved through the veins and into position for deployment of the filter. Again, this real-time ultrasonic imaging of the veins also allows for measurement of the inner diameter of the vena cava 60 for appropriate placement of the filter, and provides a visual confirmation that there is no thrombus in the area selected for deployment.

Figures 11, 12:
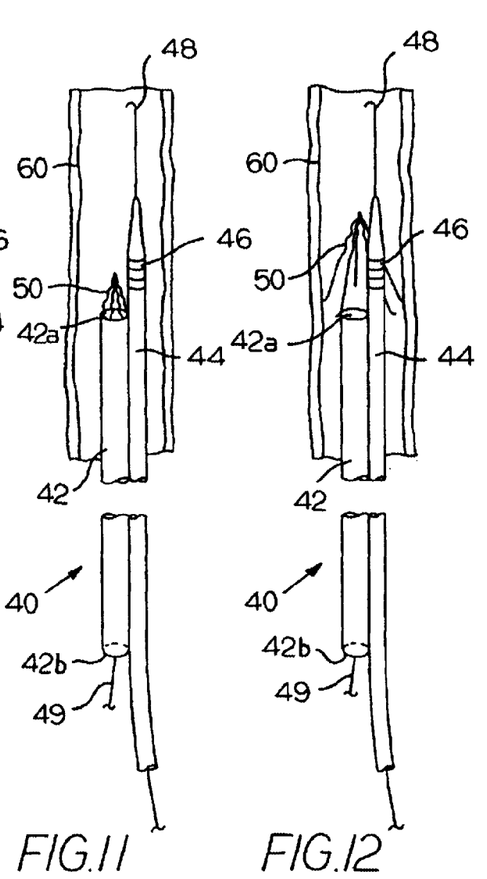
FIG. 11 illustrates insertion of and partial deployment of the vena cava filter through the deployment sheath of the preferred apparatus of FIG. 7.
FIG. 12 illustrates full deployment of the vena cava filter through the deployment sheath of the preferred apparatus of FIG. 7.

Once the apparatus 40 is appropriately positioned within the vena cava 60, the introducer 43 is withdrawn through the lower opening 42b of the deployment sheath 42, as shown in FIG. 10. Then, as shown in FIG. 11, a filter 50 and its associated delivery system 49 are inserted through the deployment sheath 42 to the appropriate location for deployment, as has been determined through ultrasonic imaging of the vena cava 60. As mentioned above, the deployment sheath 42 merely serves as a conduit into the vena cava 60 for deployment of the filter 50, and therefore the apparatus 40 of the present invention can be used with virtually any existing filter and associated delivery systems provided that the outer diameter of the deployment sheath 42 is adequate to accommodate insertion of the desired filter 50 and its associated delivery system 49.

Figure 13:
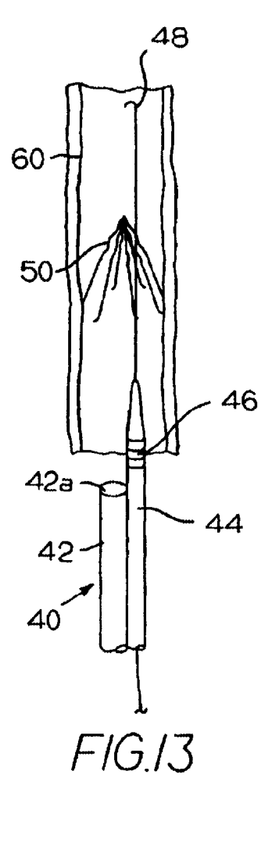
FIG. 13 illustrates the deployment sheath and ultrasonic catheter of the preferred apparatus of FIG. 7 being withdrawn from the vena cava.

FIG. 12 illustrates full deployment of the filter 50. Once so deployed, with the filter 50 in place in the vena cava 60, the deployment sheath 42 and IVUC 44 can be withdrawn, as shown in FIG. 13. As the IVUC 44 is withdrawn, the real-time ultrasonic imaging is used to evaluate the filter 50 to ensure that the struts and hooks of the filter 50 have properly attached to the walls of the vena cava 60.

Figure 14:
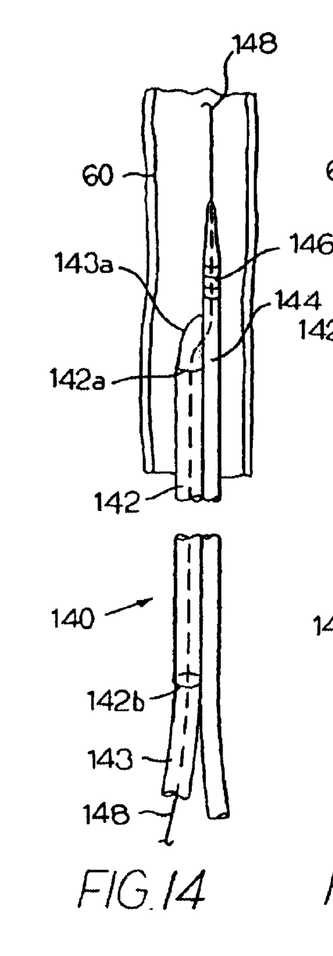
FIG. 14 illustrates a third preferred embodiment of the apparatus of the present invention being positioned in a vein for deployment of a vena cava filter, with an introducer contained within the deployment sheath of the apparatus.

FIGS. 14–18 illustrate the deployment of a filter 150 using a third preferred embodiment of the apparatus of the present invention. Referring first to FIG. 14, when the IVUC 144 and deployment sheath 142 are inserted and moved into position in the vena cava 60, it is again preferred that an introducer 143 be contained within the deployment sheath 142 to provide additional rigidity to the apparatus 140 as it is inserted and moved within the vena cava 60, and also to eliminate any sharp edges associated with the upper opening 142a of the deployment sheath 142. In this regard, the preferred introducer 143 has a rounded, smooth distal end 143a. However, in this preferred embodiment, rather than passing solely through the IVUC 144, the guide wire 148 passes through only a portion of the IVUC 144, exiting through a side wall of the IVUC 144, and then extending though the introducer 143, as indicated by a dashed line in FIG. 14. In this regard, the introducer 143 preferably has an annular cross-section and defines an inner diameter that slightly greater than the outer diameter of the guide wire 148, allowing is to be easily moved and manipulated relative to the introducer 143.

Referring still to FIG. 14, the ultrasonic imaging element 146 of the IVUC 144 extends beyond the upper opening 142a of the deployment sheath 142, or in front of the deployment sheath 142. The positioning of the ultrasonic imaging element 146 of the IVUC 144 in front of the deployment sheath 142 provides for a clear, unobstructed ultrasonic picture of the femoral vein 62 and vena cava 60 as the preferred apparatus 140 is moved through the veins and into position for deployment of the filter. Again, this real-time ultrasonic imaging of the veins also allows for measurement of the inner diameter of the vena cava 60 for appropriate placement of the filter, and provides a visual confirmation that there is no thrombus in the area selected for deployment.

Figures 15, 16, 17:
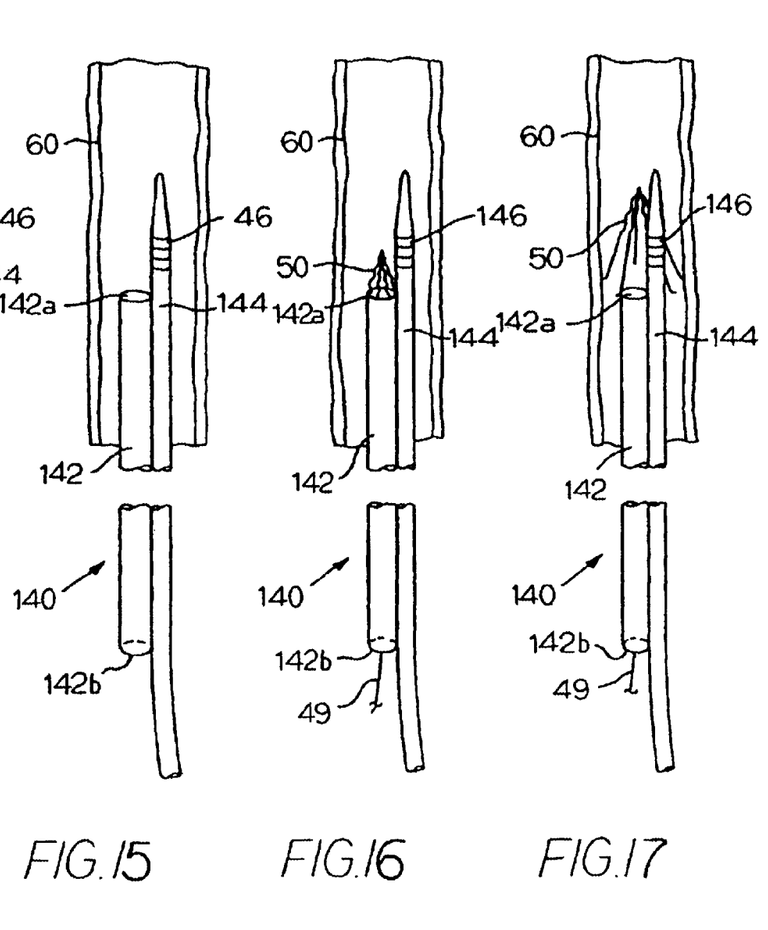
FIG. 15 illustrates the preferred apparatus of FIG. 14 after withdrawal of the introducer and guide wire from the deployment sheath of the apparatus.
FIG. 16 illustrates insertion of and partial deployment of the vena cava filter through the deployment sheath of the preferred apparatus of FIG. 14.
FIG. 17 illustrates full deployment of the vena cava filter through the deployment sheath of the preferred apparatus of FIG. 14.

Once the apparatus 140 is appropriately positioned within the vena cava 60, the introducer 143 and the guide wire 148 are withdrawn through the lower opening 142b of the deployment sheath 142, as shown in FIG. 15. Then, as shown in FIG. 16, a filter 50 and its associated delivery system 49 are inserted through the deployment sheath 142 to the appropriate location for deployment, as has been determined through ultrasonic imaging of the vena cava 60.

Figure 18:
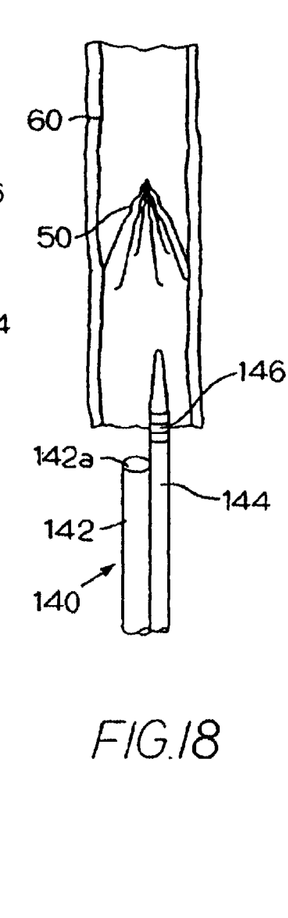
FIG. 18 illustrates the deployment sheath and ultrasonic catheter of the preferred apparatus of FIG. 14 being withdrawn from the vena cava.

FIG. 17 illustrates full deployment of the filter 50. Once so deployed, with the filter 50 in place in the vena cava 60, the deployment sheath 142 and IVUC 144 can be withdrawn, as shown in FIG. 18. As described above, as the IVUC 144 is withdrawn, the real-time ultrasonic imaging is used to evaluate the filter 50 to ensure that the struts and hooks of the filter 50 have properly attached to the walls of the vena cava 60.

Figure 19:
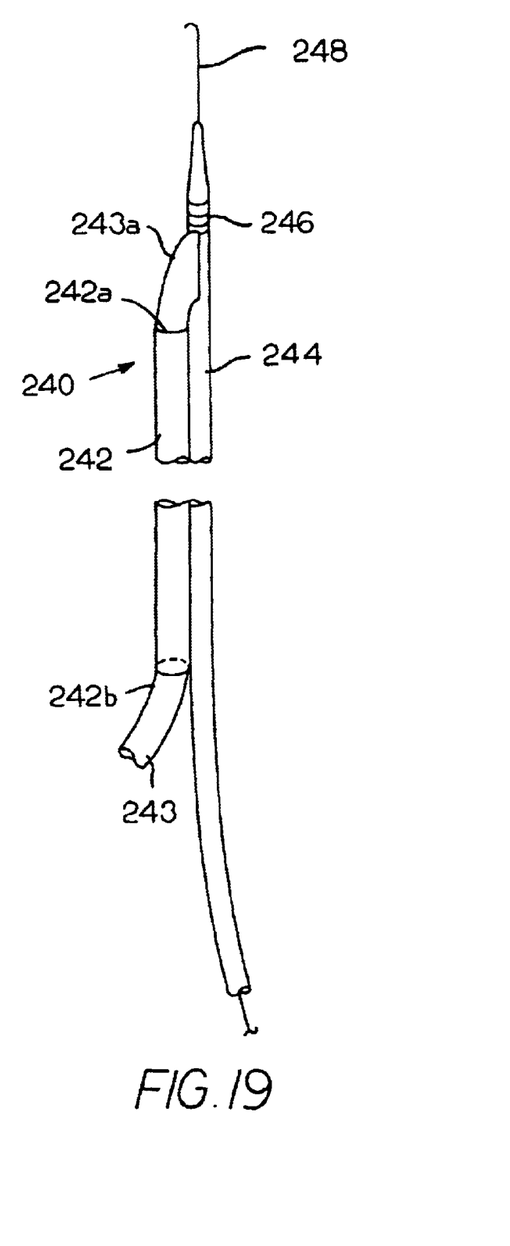
FIG. 19 illustrates a fourth preferred embodiment of the apparatus of the present invention.

FIG. 19 illustrates a fourth preferred embodiment of the apparatus of the present invention. This alternate preferred apparatus 240 is also comprised of a flexible deployment sheath 242 and an IVUC 244 with an ultrasonic imaging element 246. In this embodiment, however, the introducer 243 that is inserted into the deployment sheath 242 to provide additional rigidity to the apparatus 240 as it is inserted and moved within the vena cava, and also to eliminate any sharp edges associated with the upper opening 242a of the deployment sheath 242, has an upper portion 243a that is received in a corresponding slot or opening defined in the exterior wall of the IVUC 244. Of course, since the introducer 243 must be withdrawn from the deployment sheath 242 before insertion of a filter and its delivery system, the upper portion 243a must still have a geometry and size that allows it to be withdrawn through the deployment sheath 242.

Figure 20:
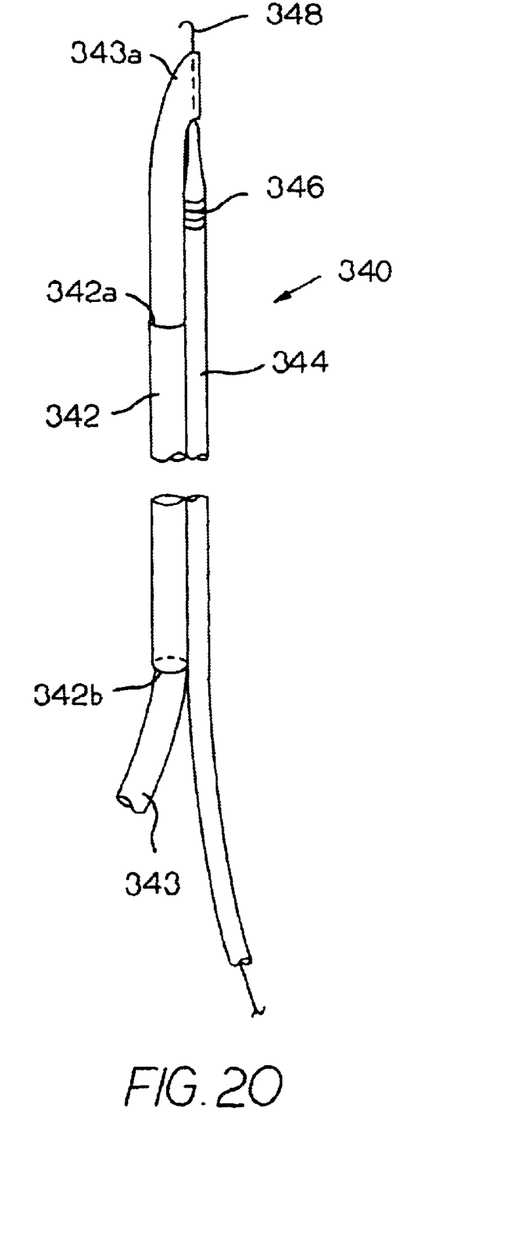
FIG. 20 illustrates a fifth preferred embodiment of the apparatus of the present invention.

FIG. 20 illustrates a fifth preferred embodiment of the apparatus of the present invention. This alternate preferred apparatus 340 is also comprised of a flexible deployment sheath 342 and an IVUC 344 with an ultrasonic imaging element 346. In this embodiment, however, the introducer 343 that is inserted into the deployment sheath 342 to provide additional rigidity to the apparatus 340 as it is inserted and moved within the vena cava, and also to eliminate any sharp edges associated with the upper opening 342a of the deployment sheath 342, has an upper portion 343a that is designed to lay over or on top of the IVUC 344. The associated guide wire 348 passes through not only the IVUC 344, but also the upper portion 343a of the introducer 343, as shown in FIG. 20. Also, as with the embodiment illustrated in FIG. 19, since the introducer 343 must be withdrawn from the deployment sheath 342 before insertion of a filter and its delivery system, the upper portion must still have a geometry and size that allows it to be withdrawn through the deployment sheath 342.

Figure 21:
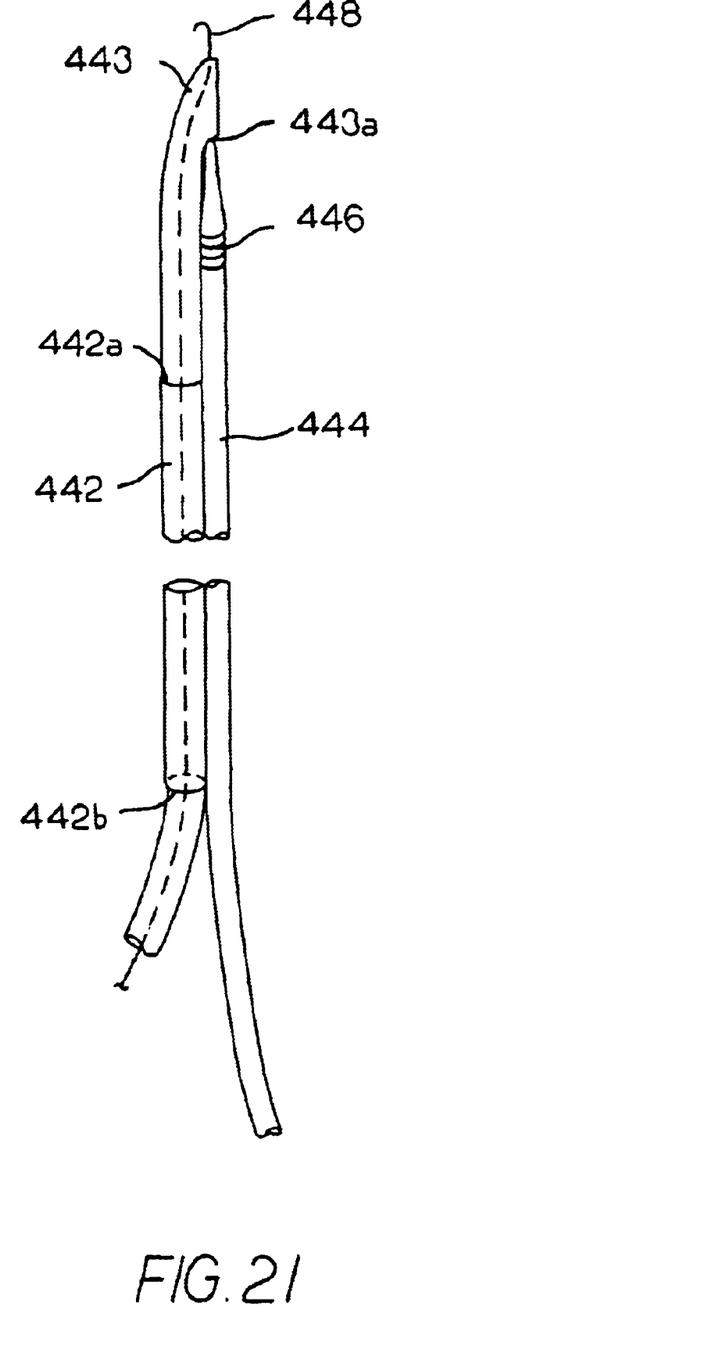
FIG. 21 illustrates a sixth preferred embodiment of the apparatus of the present invention.

FIG. 21 illustrates a sixth preferred embodiment of the apparatus of the present invention. This alternate preferred apparatus 440 is also comprised of a flexible deployment sheath 442 and an IVUC 444 with an ultrasonic imaging element 446. In this embodiment, however, the introducer 443 that is inserted into the deployment sheath 442 to provide additional rigidity to the apparatus 440 has a cut-out portion or channel 443a defined in a lateral surface of the upper portion of the introducer 443 that is adapted to receive the IVUC 444 as the apparatus 440 is inserted and moved within the vena cava. In this manner, the introducer 443 leads the IVUC 442 into the veins. Once the apparatus 440 is appropriately positioned within the vena cava, the introducer 443 can be rotated to disengage from the IVUC 444 so that it can be withdrawn through the lower opening 442b of the deployment sheath 442. Also, in the preferred embodiment, the guide wire 448 passes entirely though the introducer 443. Finally, as with the embodiments illustrated in FIGS. 19 and 20, since the introducer 443 must be withdrawn from the deployment sheath 442 before insertion of a filter and its delivery system, the upper portion must still have a geometry and size that allows it to be withdrawn through the deployment sheath 442.

The various embodiments of the apparatus of the present invention as described above could be developed and manufactured using a combination of currently available, FDA-approved intravascular ultrasound catheters, guide wire catheters, introducers and sheaths, and filters.

However, it is contemplated that other devices could be developed and used in practicing the present invention without departing from the spirit and scope of the present invention.

As the foregoing description makes clear, there are numerous advantages to the apparatus described above. A primary advantage would be the decreased cost involved in placing filters using ultrasonic imaging rather than fluoroscopy. As mentioned above, fluoroscopy procedures are extremely expensive, often requiring operating room time and specialized staffing.

Another important advantage is that the apparatus described herein are inherently safer for both patients and staff. Since x-ray equipment is not needed, the patient and staff are not exposed to the dangers of x-ray radiation. Also, an intravenous contrast is not necessary; thus, the patient is not exposed to the risk of anaphylactic shock and death from contrast reaction. Finally, since the procedures described herein can be performed at bedside, critically ill or unstable patients need not be transported. While being transported through poorly or lesser-equipped areas of a hospital, such as an elevator or the radiology suite, emergency situations, such as oxygen desaturations or arrhythmia, are more difficult to deal with because of the lack of experienced personnel and the lack of accessibility to appropriate medications and therapies.

It will be obvious to those skilled in the art that modifications may be made to the preferred embodiments described herein without departing from the spirit and scope of the present invention.

What is claimed is:

1. An apparatus for the intravascular deployment of a filter, comprising:

an intravascular ultrasound catheter, including an ultrasonic imaging element near a distal end thereof; and a deployment sheath joined to and oriented in a substantially parallel relationship with said intravascular ultrasound catheter, the ultrasonic imaging element of said intravascular ultrasound catheter extending in front of an upper opening of said deployment sheath, wherein, when said apparatus is percutaneously introduced into a vein, the ultrasonic imaging element of said intravascular ultrasound catheter generates an ultrasonic picture of the vein for identifying an appropriate location for deployment of said filter, such deployment being accomplished by inserting said filter and its delivery system through said deployment sheath to the identified appropriate location for deployment.

2. An apparatus for the intravascular deployment of a filter as recited in claim 1, in which an introducer is carried in said deployment sheath when said apparatus is percutaneously introduced into a vein, said introducer being removable to allow for insertion of said filter and its delivery system through said deployment sheath when the appropriate location for deployment of said filter is identified.

3. An apparatus for the intravascular deployment of a filter as recited in claim 2, in which said introducer has a rounded upper distal end extending beyond the upper opening of the deployment sheath.

4. An apparatus for the intravascular deployment of a filter as recited in claim 2, in which an upper distal end of said introducer is received in a corresponding slot defined in an exterior wall of said intravascular ultrasound catheter.

5. An apparatus for the intravascular deployment of a filter as recited in claim 2, and further comprising a guide wire, an upper portion of said intravascular ultrasound catheter having a substantially annular cross-section defining a central channel for the passage of said guide wire, and said introducer also having a substantially annular cross-section defining a central channel for the passage of said guide wire, said guide wire being first introduced percutaneously into said vein, the introducer, intravascular ultrasound catheter and deployment sheath being passed over said guide wire and into said vein for deployment of the filter, with the guide wire passing through the central channel defined by said introducer, through an opening defined through a side wall of said intravascular ultrasound catheter, and then passing through the central channel defined by the upper portion of said intravascular ultrasound catheter.

6. An apparatus for the intravascular deployment of a filter as recited in claim 2, and further comprising a guide wire, said introducer having a substantially annular cross-section defining a central channel for the passage of said guide wire, said guide wire being first introduced percutaneously into said vein, the introducer, intravascular ultrasound catheter and deployment sheath being passed over said guide wire, with the guide wire extending through the central channel defined by said introducer.

7. An apparatus for the intravascular deployment of a filter as recited in claim 2, in which an upper portion of said introducer extends over and above the distal end of said intravascular ultrasound catheter.

8. An apparatus for the intravascular deployment of a filter as recited in claim 7, and further comprising a guide wire, an upper portion of said introducer having a substantially annular cross-section defining a central channel for the passage of said guide wire, and said intravascular ultrasound catheter also having a substantially annular cross-section defining a central channel for the passage of said guide wire, said guide wire being first introduced percutaneously into said vein, the introducer, intravascular ultrasound catheter and deployment sheath being passed over said guide wire and into said vein for deployment of the filter with the guide wire passing through the central channel defined by said intravascular ultrasound catheter, through a distal end of said intravascular ultrasound catheter, and then passing through the central channel defined by the upper portion of said introducer.

9. An apparatus for the intravascular deployment of a filter as recited in claim 7, and further comprising a guide wire, said intravascular ultrasound catheter having a substantially annular cross-section defining a central channel for the passage of said guide wire, said guide wire being first introduced percutaneously into said vein, the introducer, intravascular ultrasound catheter and deployment sheath being passed over said guide wire and into said vein for deployment of the filter.

10. An apparatus for the intravascular deployment of a filter as recited in claim 1, and further comprising a guide wire, said intravascular ultrasound catheter having a substantially annular cross-section defining a central channel for the passage of said guide wire, said guide wire being first introduced percutaneously into said vein, the intravascular ultrasound catheter and deployment sheath of said apparatus being passed over said guide wire and into said vein for deployment of the filter.

11. An apparatus for the intravascular deployment of a filter, comprising:

an intravascular ultrasound catheter, including an ultrasonic imaging element near a distal end thereof;

a deployment sheath joined to and oriented in a substantially parallel relationship with said intravascular ultrasound catheter, the ultrasonic imaging element of said intravascular ultrasound catheter extending in front of an upper opening of said deployment sheath; and an introducer carried in said deployment sheath when said apparatus is percutaneously introduced into a vein;

wherein, when said apparatus is percutaneously introduced into a vein, the ultrasonic imaging element of said intravascular ultrasound catheter generates an ultrasonic picture of the vein for identifying an appropriate location for deployment of said filter, said introducer then being removed from said deployment sheath, and said filter and its delivery system then being inserted through said deployment sheath to the identified appropriate location for deployment of said filter.

12. An apparatus for the intravascular deployment of a filter as recited in claim 11, in which said introducer has a rounded upper distal end extending beyond an upper opening of the deployment sheath.

13. An apparatus for the intravascular deployment of a filter as recited in claim 11, and further comprising a guide wire, said guide wire being first introduced percutaneously into said vein, said apparatus being passed over said guide wire and into said vein for deployment of the filter.

14. An apparatus for the intravascular deployment of a filter as recited in claim 11, and further comprising a guide wire, an upper portion of said intravascular ultrasound catheter having a substantially annular cross-section defining a central channel for the passage of said guide wire, and said introducer also having a substantially annular cross-section defining a central channel for the passage of said guide wire, said guide wire being first introduced percutaneously into said vein, the introducer, intravascular ultrasound catheter and deployment sheath being passed over said guide wire and into said vein for deployment of the filter, with the guide wire passing through the central channel defined by said introducer, through an opening defined through a side wall of said intravascular ultrasound catheter, and then passing through the central channel defined by the upper portion of said intravascular ultrasound catheter.

15. An apparatus for the intravascular deployment of a filter as recited in claim 11, and further comprising a guide wire, said introducer having a substantially annular cross-section defining a central channel for the passage of said guide wire, said guide wire being first introduced percutaneously into said vein, the introducer, intravascular ultrasound catheter and deployment sheath being passed over said guide wire, with the guide wire extending through the central channel defined by said introducer.

16. An apparatus for the intravascular deployment of a filter as recited in claim 11, in which an upper portion of said introducer extends over and above the distal end of said intravascular ultrasound catheter.

17. An apparatus for the intravascular deployment of a filter as recited in claim 16, and further comprising a guide wire, an upper portion of said introducer having a substantially annular cross-section defining a central channel for the passage of said guide wire, and said intravascular ultrasound catheter also having a substantially annular cross-section defining a central channel for the passage of said guide wire, said guide wire being first introduced percutaneously into said vein, the introducer, intravascular ultrasound catheter and deployment sheath being passed over said guide wire and into said vein for deployment of the filter with the guide wire passing through the central channel defined by said intravascular ultrasound catheter, through a distal end of said intravascular ultrasound catheter, and then passing through the central channel defined by the upper portion of said introducer.

18. An apparatus for the intravascular deployment of a filter as recited in claim 16, and further comprising a guide wire, said intravascular ultrasound catheter having a substantially annular cross-section defining a central channel for the passage of said guide wire, said guide wire being first introduced percutaneously into said vein, the introducer, intravascular ultrasound catheter and deployment sheath being passed over said guide wire and into said vein for deployment of the filter.

* * * * *